(12) United States Patent
Cho et al.

(10) Patent No.: US 11,439,603 B2
(45) Date of Patent: Sep. 13, 2022

(54) COMPOSITIONS FOR AMELIORATING, PREVENTING OR TREATING SOMNIPATHY INCLUDING PHLOROGLUCINOL AS ACTIVE INGREDIENT AND COMPOSITIONS FOR SUPPRESSING INTOLERANCE TO OR ALLEVIATING SIDE EFFECTS OF AGONIST AT BENZODIAZEPINE BINDING SITE OF GABA-A RECEPTOR INCLUDING PHLOROGLUCINOL AS ACTIVE INGREDIENT

(71) Applicant: KOREA FOOD RESEARCH INSTITUTE, Jeollabuk-do (KR)

(72) Inventors: Sueng Mok Cho, Gyeonggido (KR); Min Young Um, Seoul (KR); Min Seok Yoon, Seoul (KR); Hye Jin Yang, Gyeonggi-do (KR); Jae Kwang Lee, Seoul (KR); Jong Hoon Jung, Gyeonggi-do (KR)

(73) Assignee: KOREA FOOD RESEARCH INSTITUTE, Jeollabuk-do (KR)

( * ) Notice: Subject to any disclaimer, the term of this patent is extended or adjusted under 35 U.S.C. 154(b) by 126 days.

(21) Appl. No.: 16/612,089

(22) PCT Filed: May 10, 2018

(86) PCT No.: PCT/KR2018/005389
§ 371 (c)(1),
(2) Date: Nov. 8, 2019

(87) PCT Pub. No.: WO2018/208107
PCT Pub. Date: Nov. 15, 2018

(65) Prior Publication Data
US 2020/0113848 A1    Apr. 16, 2020

(30) Foreign Application Priority Data

May 11, 2017   (KR) .................. 10-2017-0058387

(51) Int. Cl.
| | |
|---|---|
| *A61K 31/05* | (2006.01) |
| *A61P 25/20* | (2006.01) |
| *A61K 31/437* | (2006.01) |
| *A61K 31/496* | (2006.01) |
| *A61K 31/5025* | (2006.01) |
| *A61K 31/519* | (2006.01) |
| *A61K 9/00* | (2006.01) |

(52) U.S. Cl.
CPC ............ *A61K 31/05* (2013.01); *A61K 9/0056* (2013.01); *A61K 31/437* (2013.01); *A61K 31/496* (2013.01); *A61K 31/5025* (2013.01); *A61K 31/519* (2013.01); *A61P 25/20* (2018.01)

(58) Field of Classification Search
CPC .... A61K 31/047; A61K 31/437; A61K 31/05; A61K 31/496; A61K 31/5025; A61K 31/519; A61K 47/10; A61K 9/0019; A61K 9/0053; A61K 9/0056; A61K 9/08; A61K 9/145; A61K 9/2059; A61K 9/4858; A61P 25/20; A23V 2002/00; A23V 2200/30; A23V 2200/31; A23V 2250/30; A23L 33/10
See application file for complete search history.

(56) References Cited

FOREIGN PATENT DOCUMENTS

| JP | 2002212095 | 7/2002 | |
|---|---|---|---|
| JP | 2007217339 | 8/2007 | |
| KR | 1020120079003 | 7/2012 | |
| WO | WO-9109595 A1 * | 7/1991 | ............ A61K 31/34 |
| WO | 02/20492 | 3/2002 | |
| WO | 2012/093787 | 7/2012 | |

OTHER PUBLICATIONS

Ambien Prescribing Information, publ. 2008, pp. 1-22 (Year: 2008).*
Rauniyar et al., "Anti-Stress Activity of Phloroglucinol: A Transient Metabolite of Some Plant Polyphenolics", Pharmacologia, 2015, vol. 6, No. 1, pp. 21-30.
Landolt et al., "Zolpidem and Sleep Deprivation: Different Effect on EEG Power Spectra", J. Sleep Res., 2009, vol. 9, pp. 175-183.
Wagner et al., "Non-benzodiazepines for the treatment of insomnia", Sleep Medicine Reviews, 2000, vol. 4, No. 6, pp. 551-581.
Gericke et al., "Chronic Abuse of Zolpidem", JAMA, Dec. 14, 1994, vol. 272, No. 22, pp. 1721-1722.

* cited by examiner

*Primary Examiner* — Sarah Pihonak
(74) *Attorney, Agent, or Firm* — Duane Morris LLP; Gregory M. Lefkowitz; Brandon A. Chan

(57) ABSTRACT

The present invention relates to a pharmaceutical composition and a health functional food composition, which include phloroglucinol active ingredient, for preventing, treating, or ameliorating somnipathy and suppressing intolerance to, alleviating, or ameliorating side effects of an agonist at the benzodiazepine binding site of the GABA-A receptor. The pharmaceutical composition and the food composition rapidly and reliably induce and maintain sleep, prevent repeated awakenings, unalter physiological sleep architecture, are particularly devoid of residual sedative effects, which could impair daytime functioning and cognitive performance, and neither cause side effects nor intolerance to a conventional agonist at the benzodiazepine binding site of the GABA-A receptor despite long-term administration. The pharmaceutical composition uses a reduced amount of the agonist, which may increase the amount of sleep but degrade the quality of sleep to cause various side effects, to alleviate side effects of the agonist or suppress tolerance to the agonist resulting from long-term administration.

5 Claims, 13 Drawing Sheets

COMPOSITIONS FOR AMELIORATING, PREVENTING OR TREATING SOMNIPATHY INCLUDING PHLOROGLUCINOL AS ACTIVE INGREDIENT AND COMPOSITIONS FOR SUPPRESSING INTOLERANCE TO OR ALLEVIATING SIDE EFFECTS OF AGONIST AT BENZODIAZEPINE BINDING SITE OF GABA-A RECEPTOR INCLUDING PHLOROGLUCINOL AS ACTIVE INGREDIENT

CROSS-REFERENCE TO RELATED APPLICATIONS

This application is a § 371 national stage entry of International Application No. PCT/KR2018/005389, filed on May 10, 2018, which claims priority to Korean Patent Application No. 10-2017-0058387, filed May 11, 2017, the entire contents of which are incorporated herein by reference.

TECHNICAL FIELD

The present invention relates to a pharmaceutical composition for preventing or treating somnipathy including phloroglucinol alone or a combination of phloroglucinol and an agonist at the benzodiazepine binding site of the GABA-A receptor as an active ingredient, a pharmaceutical composition for suppressing intolerance to or alleviating side effects of an agonist at the benzodiazepine binding site of the GABA-A receptor including phloroglucinol as an active ingredient, a health functional food composition for ameliorating somnipathy including phloroglucinol as an active ingredient, and a health functional food composition for suppressing intolerance to or ameliorating side effects of an agonist at the benzodiazepine binding site of the GABA-A receptor including phloroglucinol as an active ingredient.

BACKGROUND ART

Insomnia is the most frequent sleep disorder and can be defined as a condition where a person faces problems in either initiating or maintaining sleep or both for at least three days per week while being accompanied by daytime fatigue or disturbances.

The GABA-A receptor is a pentameric protein that forms a membrane ion channel through which gamma-aminobutyric acid (GABA-A) acts. The he GABA-A receptor is closely related to the regulation of sedation, sleep, anxiety, muscle spasms, convulsion, amnesia, etc.

Agonists acting at the benzodiazepine binding site of the GABA-A receptor are classified into benzodiazepine hypnotics and non-benzodiazepine hypnotics by their structure. Diazepam is an agonist at the benzodiazepine binding site of the benzodiazepine GABA-A receptor and zolpidem, zopiclone, zaleplon, and trazodone are agonists at the benzodiazepine binding site of the non-benzodiazepine GABA-A receptor.

Zolpidem, zopiclone, zaleplon, and trazodone have the chemical names N,N,6-trimethyl-2-p-tolylimidazo[1,2-a]pyridine-3-acetamide L-(+)-tartrate (2:1), 6-(5-chloropyrid-2-yl)-5-(4-methylpiperazin-1-yl)carbonyloxy-7-oxo-6,7-dihydro-5H-pyrrolo[3,4-b]pyrazine, N-[3-(3-cyanopyrazolo[1,5-a]pyrimidin-7-yl)phenyl]-N-ethylacetamide, and 2-[3-{4-(m-chlorophenyl)-1-piperazinyl]propyl] s-triazolo[4,3-a]pyridine-3(2H)-1 monohydrochloride, respectively.

Benzodiazepine hypnotics are very effective in shortening sleep latency and prolonging sleep duration but are known to have the side effect that it is difficult to wake up on the next morning and cause daytime insomnia.

Non-benzodiazepine hypnotics shorten sleep latency and make it less difficult to wake up on the next morning than benzodiazepine hypnotics. However, possible adverse effects of non-benzodiazepine hypnotics include residual sedation and psychomotor impairment, daytime anxiety, anterograde amnesia and cognitive impairment, rebound insomnia, and drug tolerance and dependence. Patients who take non-benzodiazepine hypnotics often experience daytime drowsiness which may limit their activity and increase the danger of accidents, particularly traffic accidents.

For example, a variation in delta activity during NREM sleep is considered a physiological measure of sleep quality and depth. However, zolpidem is known to reduce the amplitude of delta waves, i.e. delta activity, or enhance high-frequency activity during slow wave sleep in the electroencephalogram (EEG), resulting in a change in sleep architecture. Although non-benzodiazepine hypnotics such as zolpidem and zopiclone were reported to be substantially devoid of the side effects found in benzodiazepine hypnotics, subsequent studies showed that these non-benzodiazepine hypnotics may produce impaired daytime psychomotor performance, pharmacological tolerance, withdrawal symptoms and be endowed with abuse potential.

Thus, there is a need to develop a drug that can achieve an optimum balance between sleep functioning and adverse effects for the treatment of insomnia. Properties of an ideal hypnotic should be a rapid and reliable sleep induction and maintenance, prevention of repeated awakenings and unaltered physiological sleep architecture. Particularly, it should be devoid of residual sedative effects, which could impair daytime functioning and cognitive performance.

The inventors of the present invention have found that phloroglucinol has much lower $IC_{50}$ and binding affinity ($K_i$) values, which represent binding and substitution effects of phloroglucinol with $GABA_A$-benzodiazepine ligand [$^3$H] flumazenil than other phlorotannins and diazepams but is effective in reducing sleep latency and increasing sleep duration when administered alone at doses of 25 to 50 mg/kg, as disclosed in Korean Patent No. 1260697.

The inventors of the present invention have also found that phloroglucinol can suppress intolerance to or alleviate side effects of a conventional agonist at the benzodiazepine binding site of the GABA-A receptor or can be used to treat somnipathy without causing side effects even when administered alone for a long period of time. The present invention has been accomplished based on these findings.

PRIOR ART DOCUMENTS

Patent Documents

Korean Patent No. 1260697

Non-Patent Documents

Landolt H P, Finelli L A, Roth C, Buck A, Achermann P, and Borbely A A. Zolpidem and sleep deprivation: different effect on EEG power spectra. J Sleep Res 2000; 9:175-83.
Wagner J and Wagner M L. Non-benzodiazepines for the treatment of insomnia. Sleep Med Rev 2000; 4:551-81.
Gericke C A and Ludolph A C. Chronic abuse of zolpidem. Jama 1994; 272:1721-2.

DETAILED DESCRIPTION OF THE INVENTION

Problems to be Solved by the Invention

The present invention is directed to providing a pharmaceutical composition for preventing or treating somnipathy including phloroglucinol as an active ingredient that rapidly and reliably induces and maintains sleep, prevents repeated awakenings, unalters physiological sleep architecture, and is particularly devoid of residual sedative effects, which could impair daytime functioning and cognitive performance.

The present invention is also directed to providing a pharmaceutical composition including phloroglucinol as an active ingredient that can alleviate side effects of an agonist at the benzodiazepine binding site of the GABA-A receptor or suppressing intolerance to the agonist resulting from long-term administration.

The present invention is also directed to providing a pharmaceutical composition for preventing or treating somnipathy including a combination of a reduced amount of an agonist at the benzodiazepine binding site of the GABA-A receptor, which may increase the amount of sleep but degrade the quality of sleep to cause various side effects, and phloroglucinol.

The present invention is also directed to providing a health functional food composition for ameliorating somnipathy including phloroglucinol as an active ingredient.

The present invention is also directed to providing a health functional food composition including phloroglucinol as an active ingredient that can alleviate side effects of an agonist at the benzodiazepine binding site of the GABA-A receptor or suppressing intolerance to the agonist resulting from long-term administration.

The present invention is also directed to providing a novel use of phloroglucinol in the preparation of a medicament for suppressing intolerance to or alleviating side effects of an agonist at the benzodiazepine binding site of the GABA-A receptor.

The present invention is also directed to providing a novel use of a combination of phloroglucinol and an agonist at the benzodiazepine binding site of the GABA-A receptor in the preparation of a medicament for treating somnipathy.

The present invention is also directed to providing a method for suppressing intolerance to or alleviating side effects of an agonist at the benzodiazepine binding site of the GABA-A receptor, including administrating phloroglucinol to a patient who has intolerance to or suffers from side effects of the agonist.

The present invention is also directed to providing a method for treating somnipathy, including administering phloroglucinol to a patient who has intolerance to or suffers from side effects of an agonist at the benzodiazepine binding site of the GABA-A receptor.

The present invention is also directed to providing a method for treating somnipathy, including administering a combination of phloroglucinol and an agonist at the benzodiazepine binding site of the GABA-A receptor to a patient with somnipathy.

Means for Solving the Problems

The present invention provides a pharmaceutical composition for preventing or treating somnipathy which includes phloroglucinol as an active ingredient and is suitable for long-term administration.

The present invention also provides a pharmaceutical composition for suppressing intolerance to or alleviating side effects of an agonist at the benzodiazepine binding site of the GABA-A receptor including phloroglucinol as an active ingredient.

The present invention also provides a pharmaceutical composition for preventing or treating somnipathy including phloroglucinol and an agonist at the benzodiazepine binding site of the GABA-A receptor as active ingredients.

The present invention also provides a health functional food composition for ameliorating somnipathy which includes phloroglucinol as an active ingredient and is suitable for long-term administration.

The present invention also provides a health functional food composition for ameliorating side effects of an agonist at the benzodiazepine binding site of the GABA-A receptor including phloroglucinol as an active ingredient.

The present invention also provides a novel use of phloroglucinol in the preparation of a medicament for suppressing intolerance to or alleviating side effects of an agonist at the benzodiazepine binding site of the GABA-A receptor.

The present invention also provides a novel use of a combination of phloroglucinol and an agonist at the benzodiazepine binding site of the GABA-A receptor in the preparation of a medicament for treating somnipathy.

The present invention also provides a method for suppressing intolerance to or alleviating side effects of an agonist at the benzodiazepine binding site of the GABA-A receptor, including administrating phloroglucinol to a patient who has intolerance to or suffers from side effects of the agonist.

The present invention also provides a method for treating somnipathy, including administering phloroglucinol to a patient who has intolerance to or suffers from side effects of an agonist at the benzodiazepine binding site of the GABA-A receptor.

The present invention also provides a method for treating somnipathy, including administering a combination of phloroglucinol and an agonist at the benzodiazepine binding site of the GABA-A receptor to a patient with somnipathy.

Effects of the Invention

The pharmaceutical composition for preventing or treating somnipathy including phloroglucinol as an active ingredient and the health functional food composition for ameliorating somnipathy including phloroglucinol as an active ingredient according to the present invention rapidly and reliably induce and maintain sleep, prevent repeated awakenings, unalter physiological sleep architecture, are particularly devoid of residual sedative effects, which could impair daytime functioning and cognitive performance, do not cause intolerance to a conventional agonist at the benzodiazepine binding site of the GABA-A receptor despite long-term administration, and do not cause side effects of a conventional agonist at the benzodiazepine binding site of the GABA-A receptor.

In addition, the pharmaceutical composition for suppressing intolerance to or alleviating side effects of an agonist at the benzodiazepine binding site of the GABA-A receptor including phloroglucinol as an active ingredient and the health functional food composition for suppressing intolerance to or ameliorating side effects of an agonist at the benzodiazepine binding site of the GABA-A receptor including phloroglucinol as an active ingredient according to the present invention can alleviate side effects of the agonist or can suppress intolerance to the agonist resulting from long-term administration.

Furthermore, the pharmaceutical composition for preventing or treating somnipathy including phloroglucinol and an agonist at the benzodiazepine binding site of the GABA-A receptor as active ingredients according to the present invention uses a reduced amount of the agonist, which may increase the amount of sleep but degrade the quality of sleep to cause various side effects, to alleviate side effects of the agonist or suppress intolerance to the agonist resulting from long-term administration.

BEST MODE FOR CARRYING OUT THE INVENTION

Figure 1:
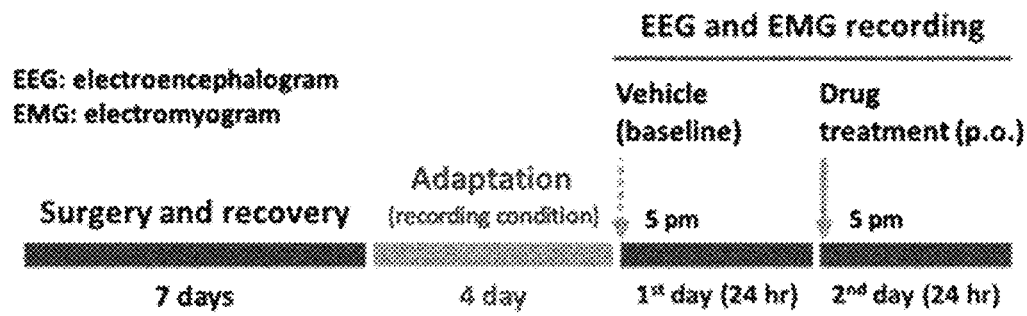
FIG. 1 is a flow diagram of an experiment for sleep architecture analysis.

The present invention is related to a pharmaceutical composition for preventing or treating somnipathy which includes phloroglucinol as an active ingredient and is suitable for long-term administration. The present invention is also related to a health functional food composition for ameliorating somnipathy which includes phloroglucinol as an active ingredient and is suitable for long-term administration.

The present invention is also related to a pharmaceutical composition for suppressing intolerance to or alleviating side effects of an agonist at the benzodiazepine binding site of the GABA-A receptor including phloroglucinol as an active ingredient. The present invention is also related to a health functional food composition for suppressing intolerance to or alleviating side effects of an agonist at the benzodiazepine binding site of the GABA-A receptor including phloroglucinol as an active ingredient.

The present invention is also related to a pharmaceutical composition for preventing or treating somnipathy including phloroglucinol and an agonist at the benzodiazepine binding site of the GABA-A receptor as active ingredients.

The expression "suitable for long-term administration" means that intolerance to an active ingredient is suppressed or side effects of the active ingredient are alleviated despite administration of the active ingredient in a therapeutically effective amount to treat somnipathy for at least 2 weeks, preferably at least 3 weeks, more preferably at least 4 weeks.

The expression "suppression of intolerance" means that the therapeutic effect on somnipathy, for example, the effect on shortening sleep latency or the effect on reducing NREM sleep duration, on the first day of administration is not statistically significant from that after administration for at least 2 weeks, preferably at least 3 weeks, more preferably at least 4 weeks; when the sleep latency on the first day of administration is defined as 100, the sleep latency is 150 or less, preferably 140 or less, more preferably 130 or less, even more preferably 120 or less, most preferably 110 or less; or when the NREM sleep duration on the first day of administration is defined as 100, the NREM sleep duration after administration is at least 80, preferably at least 85, more preferably at least 90, even more preferably at least 95, most preferably at least 100.

The expression "alleviation of side effects" means that one or more side effects selected from EEG delta power suppression and residual sedation are alleviated. The expression "alleviation of EEG delta power suppression" means that when the EEG delta power on the first day of administration is defined as 100, the EEG delta power after administration is at least 80, preferably at least 85, more preferably at least 90, even more preferably at least 95, most preferably at least 100. The expression "alleviation of residual sedation" means that no NREM sleep-enhancing effect is found after 8 hours post-administration, preferably after 7 hours post-administration, more preferably after 6 hours post-administration, even more preferably after 5 hours post-administration.

The term "somnipathy" refers to a disruptive pattern of sleep arising from numerous causes, including dysfunctional sleep mechanism, abnormalities in physiological functions during sleep, abnormalities of the biological clock, and disturbances that are induced by factors extrinsic to the sleep process. The somnipathy may be, for example, insomnia. This type of insomnia includes middle-of-the-night insomnia, late night insomnia, prolonged awakening after sleep onset insomnia, sleep maintenance insomnia, and insomnia that follows after middle-of-the-night awakening.

The agonist at the benzodiazepine binding site of the GABA-A receptor may be an agonist at the benzodiazepine binding site of the benzodiazepine GABA-A receptor or an agonist at the benzodiazepine binding site of the non-benzodiazepine GABA-A receptor. Preferred is an agonist at the benzodiazepine binding site of the non-benzodiazepine GABA-A receptor. The agonist at the benzodiazepine binding site of the non-benzodiazepine GABA-A receptor may be at least one hypnotic selected from zolpidem, zopiclone, zaleplon, and trazodone. The agonist at the benzodiazepine binding site of the non-benzodiazepine GABA-A receptor is particularly preferably a Z-drug such as zolpidem, zopiclone or zaleplon.

The content of phloroglucinol in the pharmaceutical composition for preventing or treating somnipathy including phloroglucinol as an active ingredient and suitable for long-term administration or the pharmaceutical composition for suppressing intolerance to or alleviating side effects of an agonist at the benzodiazepine binding site of the GABA-A receptor including phloroglucinol as an active ingredient is preferably determined depending on the condition and body weight of patients, the severity of the disease, the type of the drug, and the route and period of administration but can be appropriately selected by one skilled in the art. For example, phloroglucinol may be administered in an amount of 20 to 200 mg, preferably 50 to 180 mg, more preferably 80 to 160 mg, even more preferably 100 to 140 mg on a daily basis. The contents of phloroglucinol and the agonist at the benzodiazepine binding site of the GABA-A receptor as active ingredients in the pharmaceutical composition for preventing or treating somnipathy are preferably determined depending on the condition and body weight of patients, the severity of the disease, the type of the drug, and the route and period of administration but can be appropriately selected by one skilled in the art. For example, phloroglucinol may be administered in an amount of 20 to 200 mg, preferably 50 to 180 mg, more preferably 80 to 160 mg, even more preferably 100 to 140 mg, on a daily basis. For example, the daily dose of the agonist at the benzodiazepine binding site of the GABA-A receptor may be 20 to 80 parts by weight, preferably 25 to 70 parts by weight, more preferably 30 to 60 parts by weight, even more preferably 35 to 50 parts by weight, based on the daily dose (100 parts by weight) of the agonist as a single active ingredient of a pharmaceutical composition. For example, zolpidem as the agonist at the benzodiazepine binding site of the non-benzodiazepine GABA-A receptor may be administered in an amount of 2 to 10 mg, preferably 2.5 to 9 mg, more preferably 3 to 8 mg, even more preferably 3.5 to 7 mg, most preferably 4 to 6 mg, on a daily basis.

The pharmaceutical composition may be administered in single or divided doses per day but the dose is not in no way intended to limit the scope of the invention.

In pharmaceutical dosage forms of the pharmaceutical composition, the active ingredients may be administered in the form of their pharmaceutically acceptable salts or may also be used alone or in appropriate association, as well as in combination with one or more other pharmaceutically active compounds.

The pharmaceutical composition of the present invention can be formulated into oral preparations, such as powders, granules, tablets, capsules, suspensions, emulsions, syrups, and aerosols, and other preparations, such as external preparations, suppositories, and sterile injectable solutions, according to a conventional method suitable for each preparation. For appropriate formulation, the pharmaceutical composition may further include a pharmaceutically acceptable carrier, excipient or diluent known in the art.

Examples of suitable carriers, excipients or diluents include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

The pharmaceutical composition of the present invention may be formulated with diluents or excipients commonly used in the art, such as fillers, extenders, binders, wetting agents, disintegrating agents or surfactants.

Solid preparations for oral administration may be prepared by mixing the pharmaceutical composition with at least one excipient, for example, starch, calcium carbonate, sucrose, lactose or gelatin. In addition to the simple excipients, there may also be used lubricants, for example, magnesium stearate and talc.

Liquid preparations for oral administration are suspensions, solutions for internal use, emulsions, and syrups. The liquid preparations may include various excipients, for example, wetting agents, sweeteners, aromatic substances, and preservatives, as well as simple diluents known in the art, such as water and liquid paraffin.

Sterilized aqueous solutions, non-aqueous solvents, suspensions, emulsions, lyophilizates, and suppositories are included in preparations for parenteral administration. The non-aqueous solvents and the suspensions may be propylene glycol, polyethylene glycol, vegetable oils such as olive oil, and injectable esters such as ethyl oleate. Witepsol, Macrogol, Tween 61, cacao butter, laurin butter, and glycerogelatin may be used as bases of the suppositories.

The pharmaceutical composition of the present invention can be formulated according to the type of diseases or the kind of ingredients in accordance with any suitable method known in the art, preferably, any of the methods disclosed in Remington's Pharmaceutical Science, Mack Publishing Company, Easton Pa.

The pharmaceutical composition of the present invention can be administered to mammals, including rats, mice, livestock, and humans, via various routes. All routes of administration may be contemplated. The pharmaceutical composition of the present invention may be administered by any suitable route, for example, orally, rectally, intravenously, intramuscularly, subcutaneously, intrauterinely or intracerebroventricularly.

The health functional food composition of the present invention is formulated in the same manner as described for the pharmaceutical composition. The health functional food composition of the present invention per se may be used as a health functional food. Alternatively, the active ingredient may be added to various food products, for example, beverages, alcoholic beverages, confectionery, diet bars, dairy products, meats, chocolates, pizzas, instant noodles, other noodles, chewing gums, ice creams, vitamin complexes, and health supplement foods.

In addition to phloroglucinol as the active ingredient, the health functional food composition may optionally further include one or more ingredients that are usually added for food production. For example, the optional ingredients may be selected from proteins, carbohydrates, fats, nutrients, seasoning agents, and flavoring agents. Examples of the carbohydrates include: saccharides, such as monosaccharides (e.g., glucose and fructose), disaccharides (e.g., maltose, sucrose, and oligosaccharides), and polysaccharides (e.g., dextrin and cyclodextrin); and sugar alcohols, such as xylitol, sorbitol, and erythritol. Natural flavoring agents, such as thaumartin and stevia extracts (e.g., rebaudioside A and glycyrrhizin) and synthetic flavoring agents (e.g., saccharin and aspartame) may be used. For example, the food composition of the present invention may be prepared into a drink or beverage. In this case, the food composition of the present invention may further include citric acid, high fructose corn syrup, sugar, glucose, acetic acid, malic acid, fruit juice, and a plant extract, in addition to the active ingredient.

The term "health functional food" refers to a food that is produced by adding phloroglucinol to a food material such as a beverage, tea, spice, chewing gum or cookie or by preparing phloroglucinol into a capsule, powder or suspension. The intake of the health functional food brings about the desired healthy effect. The health functional food causes no side effects when taken for a long period of time, unlike general medicines, because it uses a food as a raw material. The health functional food is very useful because its routine intake is possible. The content of phloroglucinol in the health functional food varies depending on the kind of the health functional food and is thus not uniformly determined. The content of phloroglucinol is not particularly limited so long as phloroglucinol does not change the original taste of the food. Phloroglucinol is typically added in an amount of 0.001 to 50% by weight, preferably 0.01 to 20% by weight, more preferably 0.1 to 10% by weight, based on the weight of the desired food. In the case of the health functional food in the form of a pill, granule, tablet or capsule, phloroglucinol is typically added in an amount of 0.1 to 100% by weight, preferably 0.2 to 80% by weight, more preferably 0.5 to 50% by weight. For example, the health functional food may take the form of a pill, tablet, capsule or beverage.

The present invention will be explained in more detail with reference to the following examples. It will be evident to those skilled in the art that these examples are not intended to limit the scope of the present invention.

Experimental Example 1: Sleep Architecture Analysis after Single Administration

1) Preparation of Experimental Animals

C57BL/6N mice (28-30 g, 12-week old male) were received from Koatech Co. Ltd. (Pyeongtaek, Gyeonggi-do, Korea) and acclimated to the vivarium for a period of one week before testing was conducted. The animals were housed at a temperature of 23±1° C., a humidity of 55±5%, and a light intensity of 3000 Lux under a 12 h light-dark cycle (light on from 07:00 to 19:00). The animals had ad libitum access to food and water. All animals were maintained in accordance with the guidelines for the Institutional Animal Care and Use Committee of the Korea Food Research Institute (KFRI-IACUC).

2) Procedure for Sleep Architecture Analysis

A flow diagram of an experiment for sleep architecture analysis is shown in FIG. 1.

C57BL/6N mice were acclimated for a period of one week and received electrode implantation for electroencephalogram (EEG) and electromyogram (EMG) recordings. Each mouse was anesthetized with pentobarbital (50 mg/kg, i.p.) and its head was fixed in a stereotaxic instrument. After the subcutaneous connective tissue of the head was incised, an EEG/EMG headmount (Pinnacle Technology Inc., Lawrence, Kans., USA) was implanted for EEG and EMG recordings, fixed with dental cement, and closed with sutures. The surgical site was sterilized and an antibiotic was administered for 3 days to prevent possible inflammation after surgery. The animal was allowed to recover for 7 days. For adaptation to the recording conditions, 0.5% CMC-saline solution used as a control was administered orally from 4 days before measurement. Thereafter, the recording instrument was connected to induce acclimation of the animal to this experimental procedure.

After oral administration of a sample, the animal was stabilized for 5 min. Then, EEG and EMG were recorded using PAL-8200 series (Pinnacle Technology Inc., Lawrence, Kans., USA) for 24 h from 17:00. The sampling rate for EEG and EMG recordings was set to 200 Hz (epoch time: 10 s). The filtering range was set to 0.1-25 Hz for EEG data recording and 10-100 Hz for EMG data recording.

Figure 2:
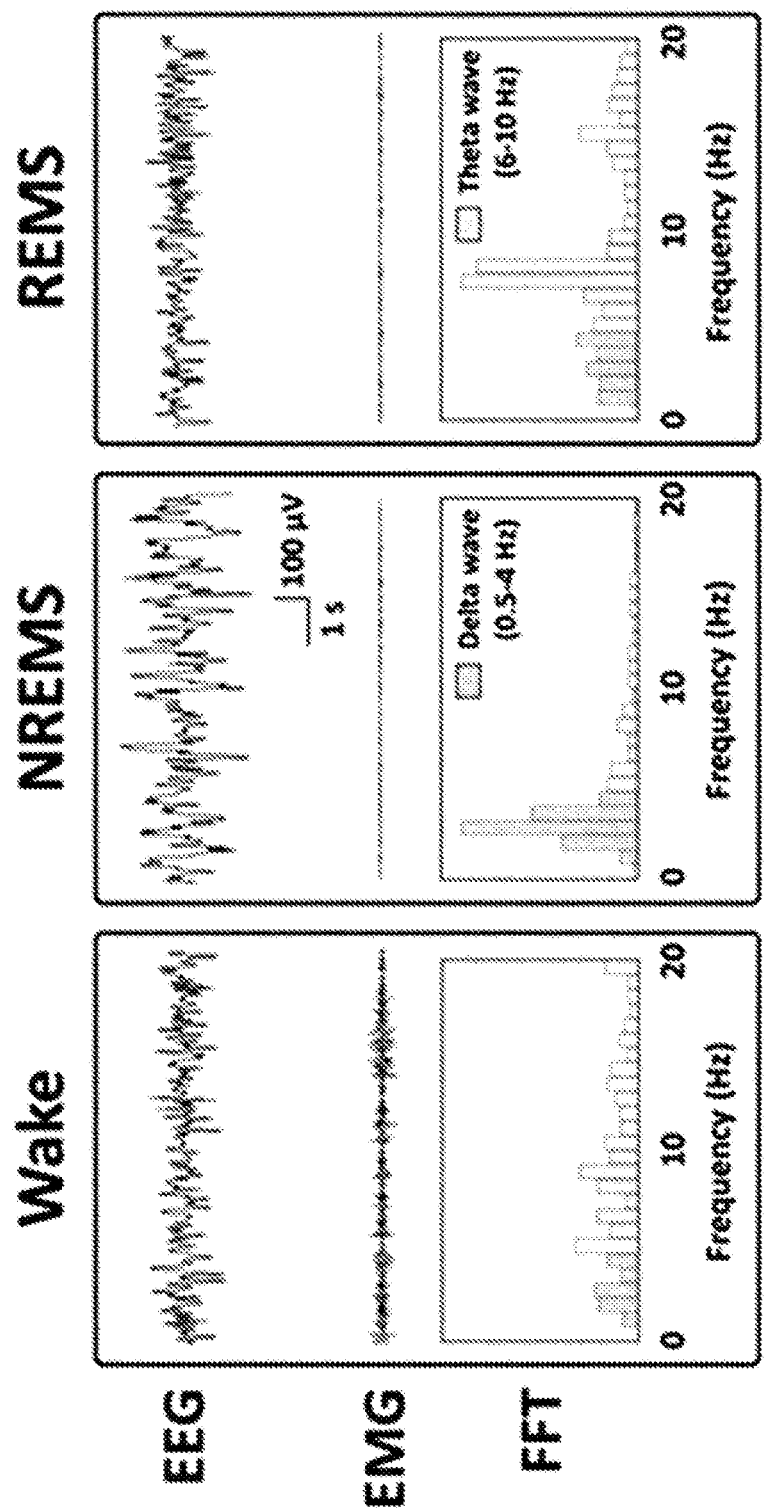
FIG. 2 shows typical EEG and EMG waveforms and FFT spectra of a mouse in the Wake, REMS, and NREMS.

Sleep architecture analysis was conducted according to the fast Fourier transform (FFT) algorithm using the SleepSign program (Ver. 3.0, Kissei Comtec Inc., Matsumoto, Nagono, Japan). Typical EEG and EMG waveforms and FFT spectra of a mouse in the Wake, REMS, and NREMS are shown in FIG. 2.

The results were divided into three stages: Wake, REMS (rapid eye movement sleep, theta band: 6-10 Hz) and NREMS (non-rapid eye movement sleep, delta band: 0.5-4 Hz). Sleep latency was defined as the time required for NREM sleep with 10 s epoch to occur consecutively at least 12 times (Blanco-Centurion et al., 2006). The values in the 0.5-4 Hz range were averaged and the delta power during NREM sleep was expressed in percent relative to the control.

All animal experimental data were expressed as mean±standard deviation. The significant difference between two groups was evaluated by t-test and the levels of significance were set as $p<0.05(*)$ and $p<0.01(**)$. The asterisks indicate significant differences.

Figure 3:
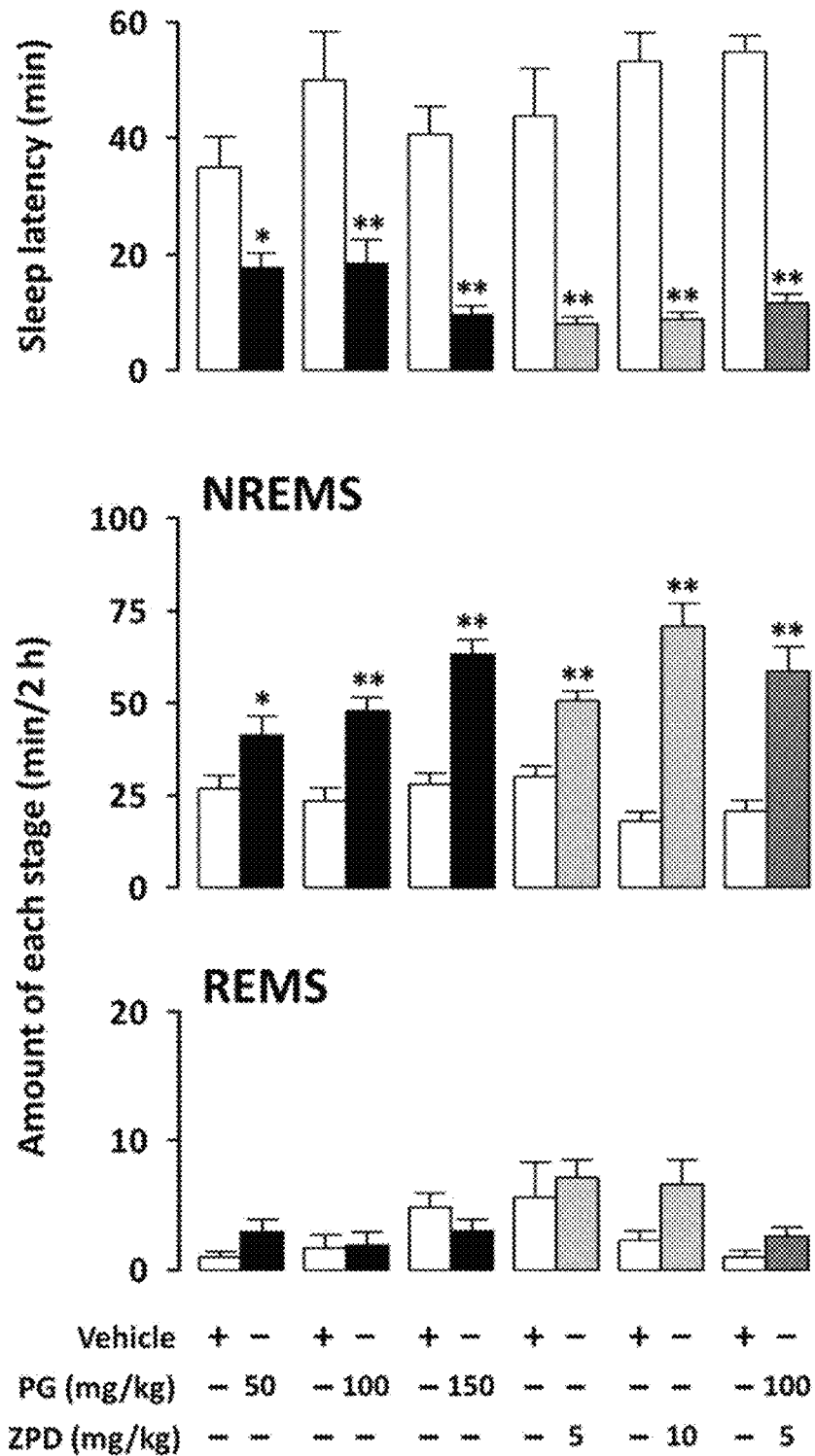
FIG. 3 shows effects of phloroglucinol (PG), zolpidem (ZPD), and a combination of phloroglucinol and zolpidem with and without a negative control (vehicle) on sleep latency and sleep architecture when administered at different concentrations in Experimental Example 1.

3) Effects on Reducing Sleep Latency and Variations in Sleep Architecture after Single Administration The sleep latencies of the group administered orally with phloroglucinol (PG) were significantly reduced at all concentrations (50, 100 and 150 mg/kg) compared to those of the negative control (vehicle). Zolpidem (ZPD), a representative non-benzodiazepine hypnotic, significantly reduced sleep latencies at concentrations of 5 and 10 mg/kg (see FIG. 3).

The group co-administered phloroglucinol (100 mg/kg) and zolpidem (5 mg/kg) had a sleep latency by ~40 min shorter than that of the control group. In addition, the co-administration showed a similar reducing effect on sleep latency to the single administration of zolpidem (10 mg/kg), which reduced sleep latency by ~44 min.

Meanwhile, EEGs were recorded for 2 h after oral administration of the negative control, phloroglucinol, zolpidem, and the combination of phloroglucinol and zolpidem to C57BL/6N mice. The recorded EEGs were analyzed to investigate sleep architecture and sleep duration. As a result, phloroglucinol and zolpidem increased NREM sleep in a concentration-dependent manner without affecting REM sleep (see FIG. 3).

Zolpidem significantly increased NREM sleep duration by 40.8% and 74.6% at concentrations of 5 and 10 mg/kg, respectively ($p<0.01$). The NREM sleep duration of the group co-administered phloroglucinol (100 mg/kg) and zolpidem (5 mg/kg) was increased by 64.6% ($p<0.01$), which did not reach the effect obtained with 10 mg/kg zolpidem but was better than the effect of 5 mg/kg zolpidem on sleep enhancement.

4) Variation in Delta Activity after Single Administration

A variation in delta activity during NREM sleep is considered a physiological measure of sleep quality and depth (Bastien et al., 2003; Chen et al., 2012). It was reported that zolpidem reduces sleep latency and increases the amount of sleep but reduces delta activity during NREM sleep (Kopp et al., 2004; Alexandre et al., 2008).

Figure 4:
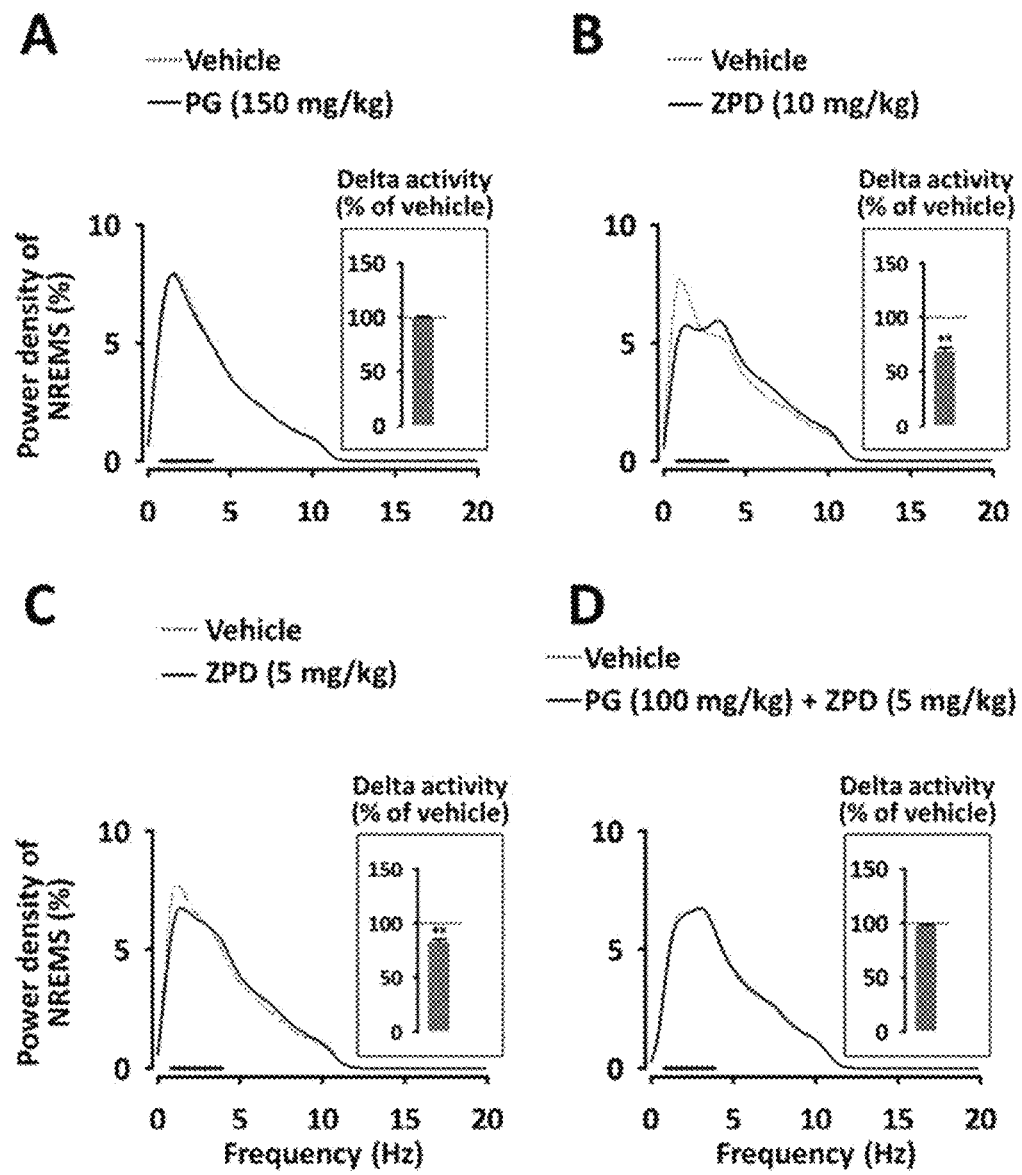
FIG. 4 shows delta activities when phloroglucinol (PG, 150 mg/kg), zolpidem (ZPD, 10 mg/kg and 5 mg/kg), and a combination of phloroglucinol (100 mg/kg) and zolpidem (5 mg/kg) were administered in Experimental Example 1.

Not only the oral administration of 10 mg/kg zolpidem but also the oral administration of a half amount (5 mg/kg) zolpidem was found to significantly reduce delta activity in the range of 0.5-4 Hz ($p<0.01$) (see FIG. 4). Due to its typical property to reduce delta activity, zolpidem increased the amount of NREM sleep but degraded sleep architecture and sleep quality.

However, there was no significant change in delta activity in the group administered orally with up to 150 mg/kg phloroglucinol alone, demonstrating that phloroglucinol induces physiological sleep without degrading the quality of sleep, unlike zolpidem (see FIG. 4).

Unlike the significant reduction in delta activity by administration of 5 mg/kg zolpidem, no change in delta activity was found in the group co-administered phloroglucinol (100 mg/kg) and zolpidem (5 mg/kg) (see FIG. 4). These results concluded that phloroglucinol is effective in enhancing sleep while suppressing the side effects of zolpidem that reduces delta activity to alter sleep architecture and degrade the quality of sleep.

Meanwhile, like the administration of zolpidem, the administration of 5 mg/kg diazepam significantly reduced delta activity in the range of 0.5-4 Hz, leading to a degradation in the quality of sleep. In contrast, administration of a combination of 100 mg/kg phloroglucinol and 5 mg/kg diazepam caused no change in delta activity (data not shown). These results concluded that phloroglucinol is effective in enhancing sleep while suppressing the side effects of diazepam that reduces delta activity to alter sleep architecture and degrade the quality of sleep.

5) Time-Dependent Changes in Sleep Architecture after Single Administration

Figure 5:
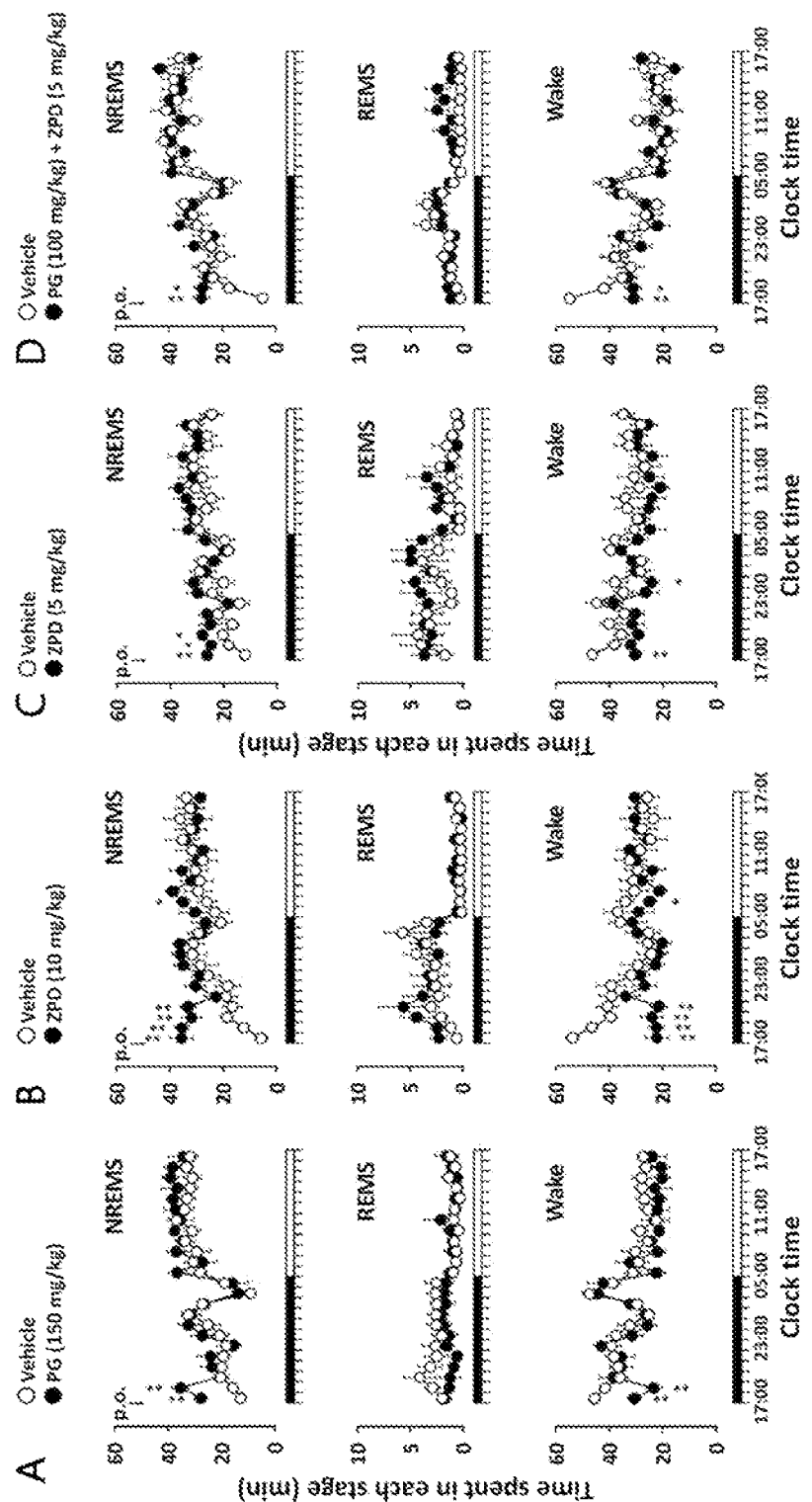
FIG. 5 shows time-dependent changes in sleep architecture after administration of phloroglucinol (PG, 150 mg/kg), zolpidem (ZPD, 10 mg/kg and 5 mg/kg), and a combination of phloroglucinol (100 mg/kg) and zolpidem (5 mg/kg) in Experimental Example 1.

After oral administration of the negative control, phloroglucinol, zolpidem, and the combination of phloroglucinol and zolpidem, time-dependent changes in sleep architecture were investigated (see FIG. 5).

The single administration of 150 mg/kg phloroglucinol significantly increased NREM sleep only for the first 2 h, and thereafter, it showed a tendency similar to the administration of the control (A of FIG. 5). In contrast, when 10 mg/kg zolpidem alone was administered, a sleep-enhancing effect lasted for the first 4 h and NREM sleep was significantly increased even at 14 h after administration, demonstrating the residual sedative effect of zolpidem (B of FIG. 5).

The administration of a half dose (5 mg/kg) of zolpidem significantly increased NREM sleep for the first 3 h and significantly reduced vigilance for up to 9 h after administration, resulting in a slight residual sedation (see C of FIG. 5). In contrast, a sleep-enhancing effect was observed only for the first 2 h in the group co-administered with 100 mg/kg phloroglucinol and 5 mg/kg zolpidem, as in the group administered with 150 mg/kg phloroglucinol alone. No residual sedative effect was found in the group co-administered with 100 mg/kg phloroglucinol and 5 mg/kg zolpidem, unlike in the groups administered with 10 mg/kg and 5 mg/kg zolpidem alone (see D of FIG. 5).

Experimental Example 2: Mechanism of Action for Sleep Enhancement

To investigate the mechanism of action for sleep enhancement, flumazenil, an antagonist of the $GABA_A$-benzodiazepine receptor, was administered 15 min before oral administration of phloroglucinol and EEG and EMG were recorded by the same method as described in Experimental Example 1.

Zolpidem is a $GABA_A$-benzodiazepine receptor agonist and its sleep-enhancing effect is known to be suppressed by flumazenil. In this example, zolpidem was used as a positive control.

Figure 6:
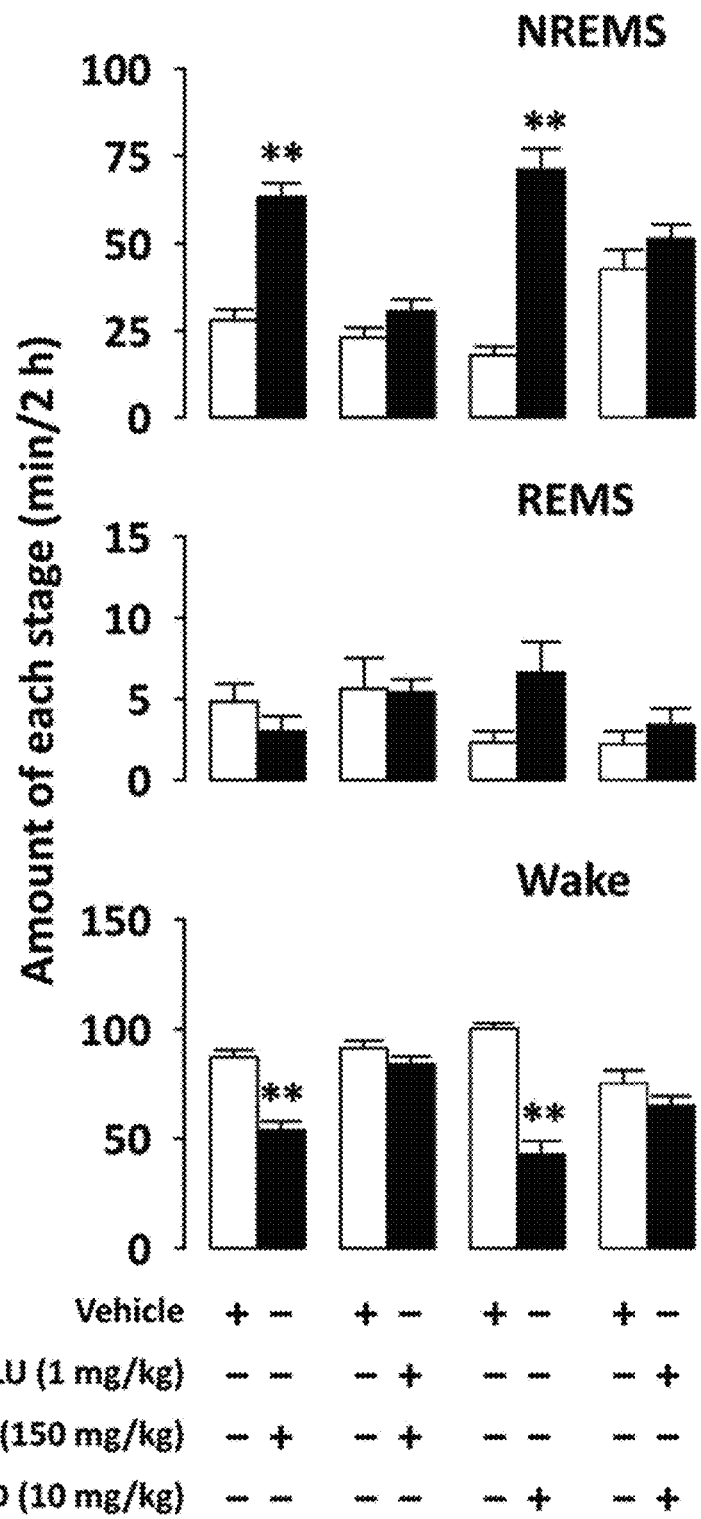
FIG. 6 shows the results of sleep architecture analysis after administration of flumazenil, an antagonist of the $GABA_A$-benzodiazepine receptor, 15 minutes before oral administration of phloroglucinol to confirm the mechanism of action for sleep enhancement in Experimental Example 2.

The sleep-enhancing effect of zolpidem was completely blocked by flumazenil (see FIG. 6). Phloroglucinol increased NREM sleep when untreated with flumazenil but the treatment with flumazenil reduced the amount of NREM sleep of the group treated with phloroglucinol to a level similar to that of a negative control (vehicle) (see FIG. 6).

Figure 7:
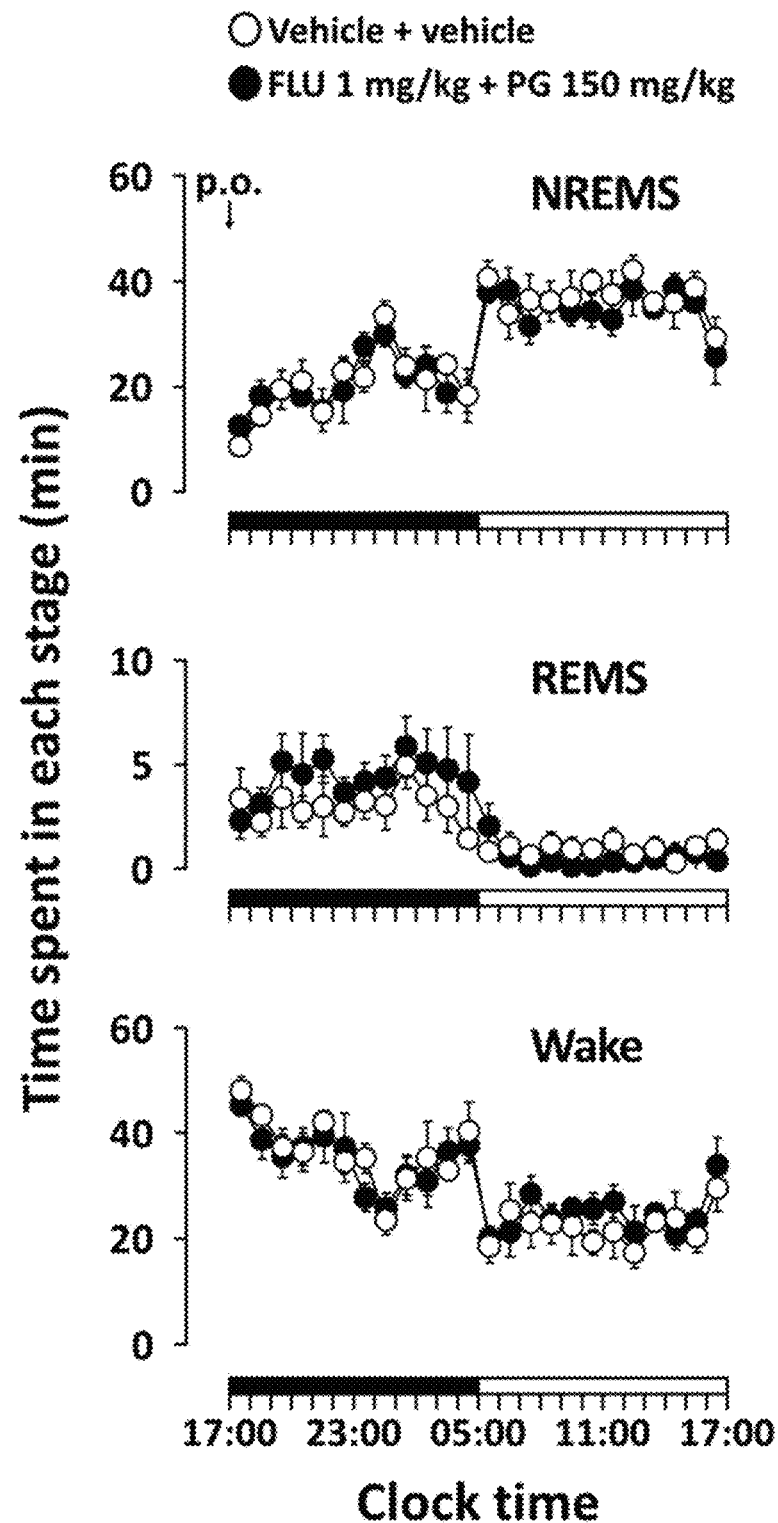
FIG. 7 shows time-dependent changes in sleep architecture after administration of flumazenil, an antagonist of the $GABA_A$-benzodiazepine receptor, 15 minutes before oral administration of phloroglucinol to confirm the mechanism of action for sleep enhancement in Experimental Example 2.

Time-dependent changes in sleep architecture were analyzed in the same manner as described in Experimental Example 1. As a result, when flumazenil was administered, the phloroglucinol-administered group had similar sleep architecture to the negative control (see FIG. 7). These results reveal that phloroglucinol as a $GABA_A$-benzodiazepine receptor agonist can enhance sleep.

Experimental Example 3: Sleep Architecture During Long-Term Administration

1) Experimental Method

Figure 8:
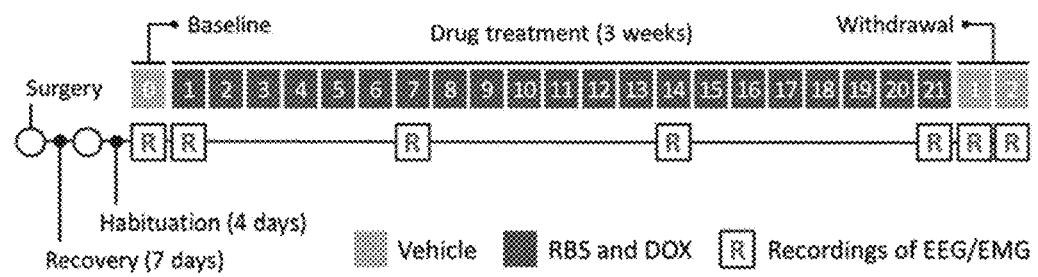
FIG. 8 is a flow diagram of an experiment for recording the EEG of a mouse during long-term administration.

Experimental animals were prepared and their sleep architecture was analyzed in the same manner as in Experimental Example 1. As in the single administration in Experimental Example 1, the mice were allowed to recover for 7 days after surgery and acclimated for 4 days. Thereafter, baselines (BL) were measured on day 0 after acclimation and a sample was administered orally to each animal for 21 days. EEGs were recorded on days 1, 7, 14, and 21. EEGs were recorded and analyzed during the subsequent 2-day withdrawal. FIG. 8 is a flow diagram of an experiment for sleep architecture analysis during long-term administration. The samples were 100 mg/kg phloroglucinol (PG), 5 mg/kg zolpidem (ZPD), and a combination of 100 mg/kg phloroglucinol and 5 mg/kg zolpidem, which were administered once daily.

2) Effect on Shortening Sleep Latency and Change in Sleep Architecture During Long-Term Administration Zolpidem (ZPD) was reported to cause side effects such as intolerance when taken for a long period of time such as 3 weeks or longer (Steppuhn et al., 1992; Priest et al., 1997; Ebert et al., 2008). This experiment was conducted to confirm whether 1) the long-term administration of the combination of phloroglucinol (PG) and zolpidem suppressed side effects previously reported for zolpidem and 2) the long-term administration of phloroglucinol alone showed similar intolerance to that of zolpidem and caused side effects observed for zolpidem. EEGs were recorded for the mice on days 0, 1, 7, 14, and 21 during long-term administration of each sample for 3 weeks. The recorded EEGs were analyzed.

During the oral administration of zolpidem (5 mg/kg) alone for 3 weeks, a significant reduction in sleep latency and a significant increase in NREM sleep duration were observed compared to the corresponding baselines (BL). However, the administration of zolpidem showed a tendency to increase sleep latency with increasing administration period. There was a significant difference in sleep latency between at the third week and on the first day after administration, demonstrating intolerance to zolpidem in the experimental animals. Further, the administration of zolpidem showed a tendency to reduce NREM sleep duration with increasing administration period. There was a significant difference in NREM sleep duration between at the third week and on the first day after administration, demonstrating intolerance to zolpidem in the experimental animals (see FIG. 9).

These results can lead to the conclusion that the long-term administration (>3 weeks) of zolpidem gradually diminishes its effects on shortening sleep latency and on prolonging NREM sleep duration.

During the oral administration of phloroglucinol (100 mg/kg) alone for 3 weeks, a significant reduction in sleep latency and an increase in NREM sleep duration were observed compared to the corresponding baselines (BL). However, the significantly reduced sleep latency compared to the baseline on day 1 remained unchanged even on days 7, 14, and 21. Further, the increased NREM sleep duration on day 1 persisted up to day 21, revealing that phloroglucinol caused no intolerance despite long-term administration, unlike zolpidem (see FIG. 9).

Figure 9:
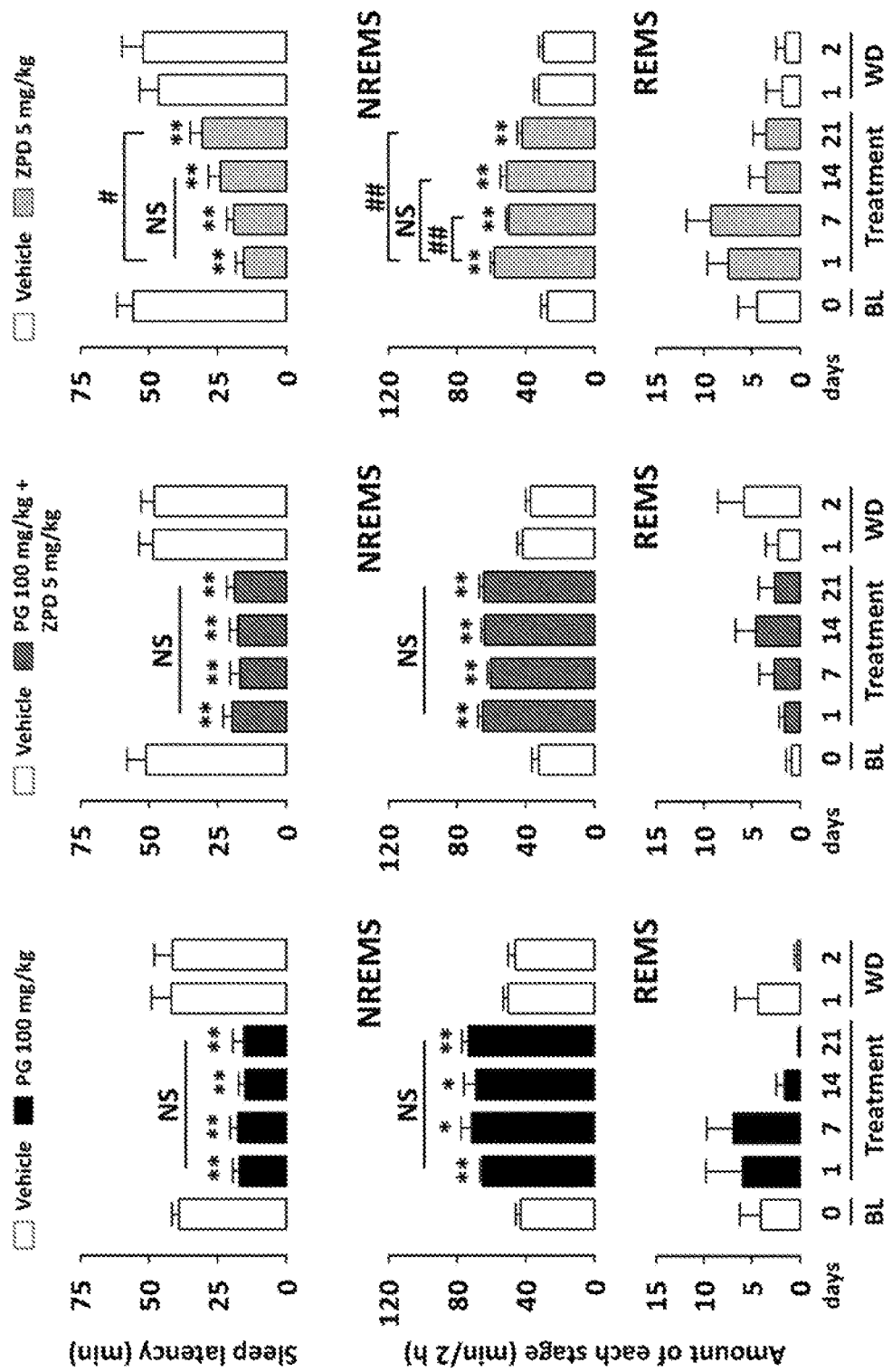
FIG. 9 shows effects of 100 mg/kg phloroglucinol (PG), 5 mg/kg zolpidem (ZPD), and a combination of 100 mg/kg phloroglucinol and 5 mg/kg zolpidem on sleep latency and sleep architecture on different days during long-term administration and on different days after withdrawal in Experimental Example 3.

The effect on shortening sleep latency and the effect on prolonging NREM sleep duration were gradually diminished during the single administration of zolpidem (5 mg/kg), but none of these phenomena were observed during the combined administration of phloroglucinol (100 mg/kg) and zolpidem (5 mg/kg) (see FIG. 9). These results can lead to the conclusion that phloroglucinol suppresses intolerance caused by long-term administration of zolpidem or reduces the incidence of side effects of zolpidem during long-term administration.

In all experimental groups, there were significant differences in sleep latency and NREM sleep duration compared to the corresponding baselines during the withdrawal period (see FIG. 9).

3) Chances in NREM Sleep Duration During Long-Term Administration

Figure 10A:
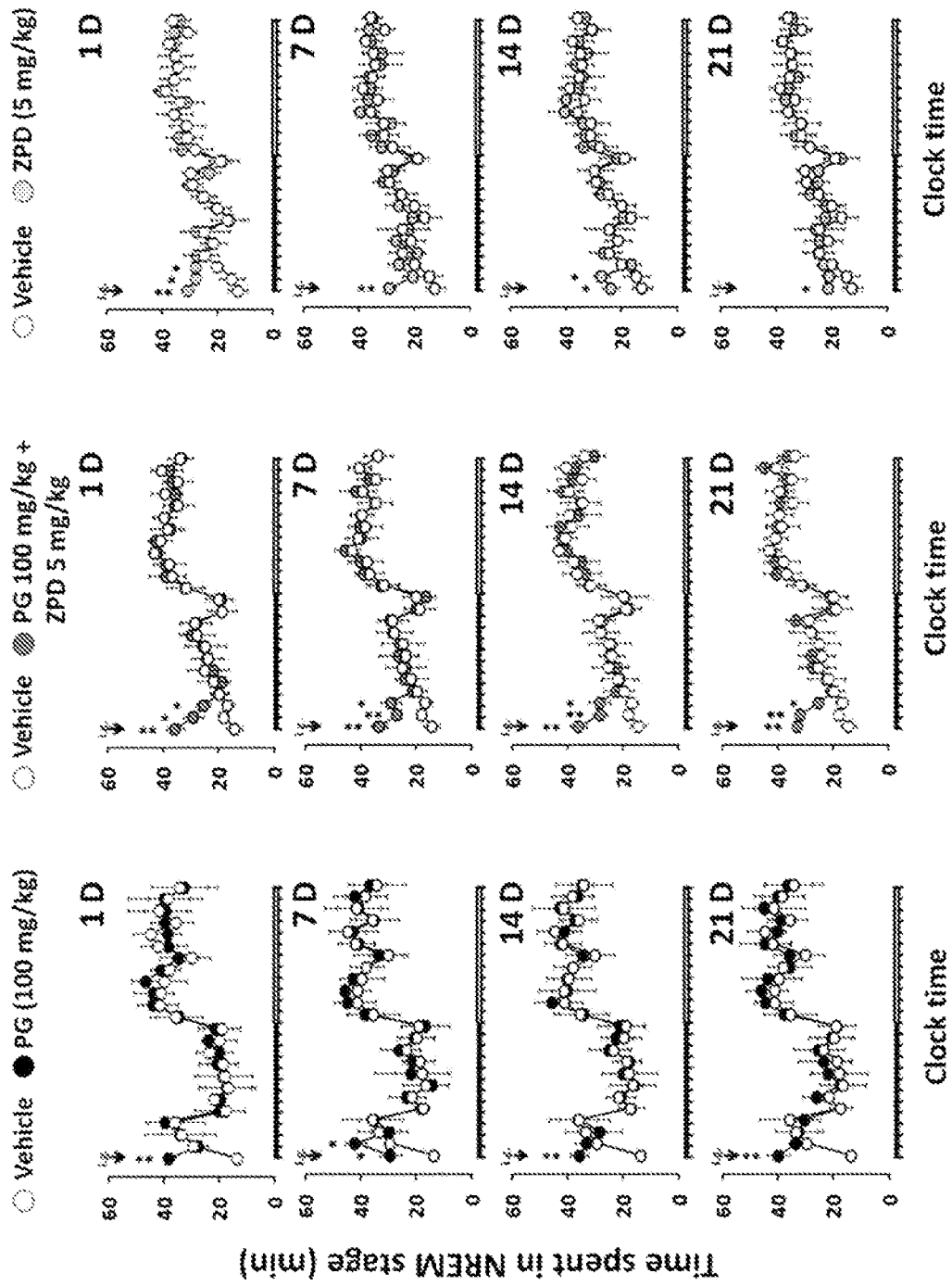
FIG. 10A shows changes in NREM sleep duration on different days during long-term administration of 100 mg/kg phloroglucinol (PG), 5 mg/kg zolpidem (ZPD), and a combination of 100 mg/kg phloroglucinol and 5 mg/kg zolpidem in Experimental Example 3.
Figure 10B:
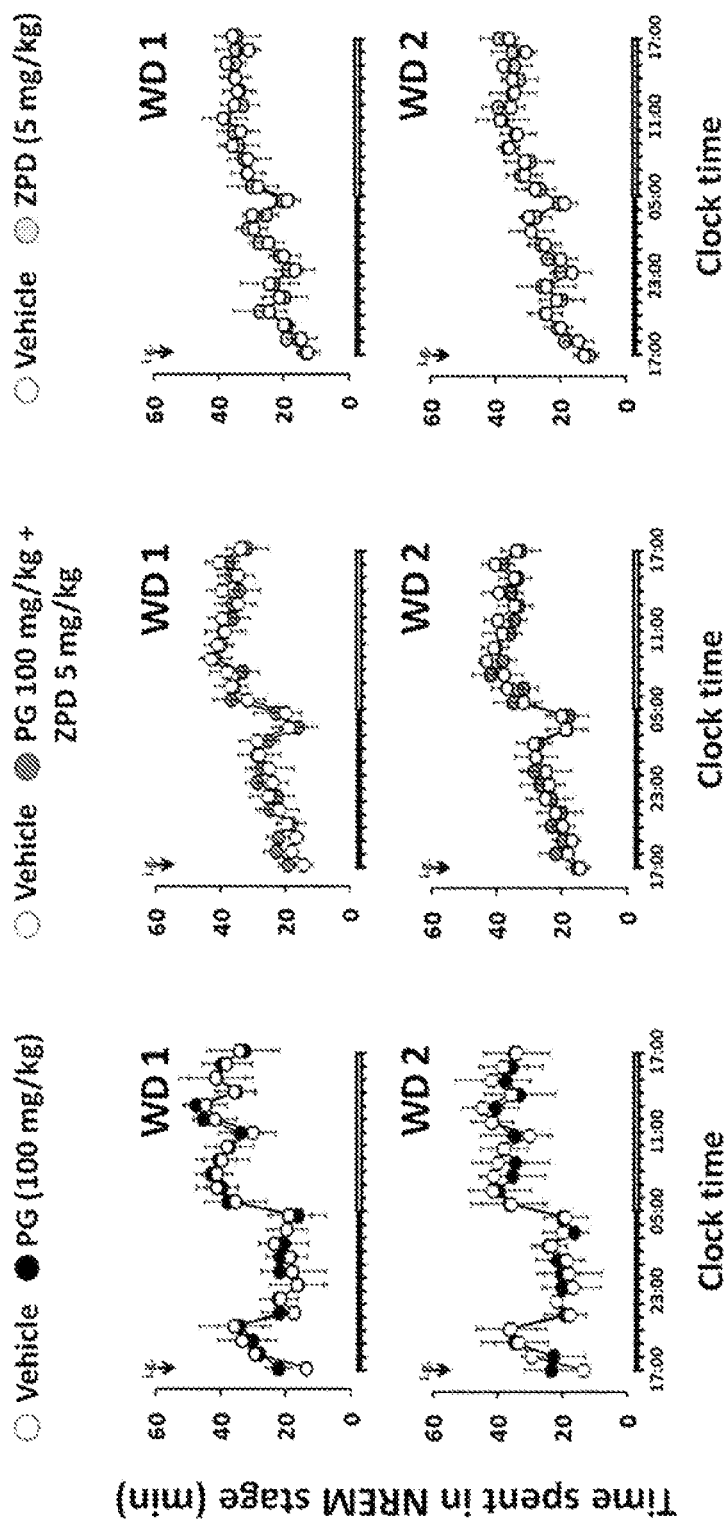
FIG. 10B shows time-dependent changes in NREM sleep duration after withdrawal of long-term administration of 100 mg/kg phloroglucinol (PG), 5 mg/kg zolpidem (ZPD), and a combination of 100 mg/kg phloroglucinol and 5 mg/kg zolpidem in Experimental Example 3.

Time-dependent changes in NREM sleep duration on days 1, 7, 14, and 21 during long-term administration for 3 weeks and during subsequent withdrawal (WD) are shown in FIGS. 10A and 10B, respectively.

The single administration of zolpidem (5 mg/kg) led to a significant increase in NREM sleep duration for the first 3 h on day 1 compared to the baseline but the effect was gradually diminished thereafter. A significant increase in NREM sleep duration was found only for the first 1 h on day 21.

In contrast, phloroglucinol (100 mg/kg) was not effective in enhancing NREM sleep when administered alone compared to zolpidem but its NREM sleep-enhancing effect lasted similarly from day 1 to day 21, revealing that phloroglucinol did not cause any intolerance.

Particularly, the combined administration of phloroglucinol (100 mg/kg) and zolpidem (5 mg/kg) was effective in enhancing NREM sleep for the first 3 h compared to the single administration of phloroglucinol (5 mg/kg). In addition, when phloroglucinol (100 mg/kg) and zolpidem (5 mg/kg) were co-administered, the significantly increased NREM sleep duration for the first 3 h on day 1 lasted even on days 7, 14, and 21, unlike when zolpidem (5 mg/kg) was administered alone. That is, it was found that the co-administration of phloroglucinol and zolpidem maintains its effect on increasing NREM sleep duration for a long period of time.

Meanwhile, in all experimental groups, the increased NREM sleep durations during administration of the samples were found to be similar to the corresponding baselines during the withdrawal period.

4) Chances in Delta Activity During Long-Term Administration

As found after the single administration of zolpidem (5 mg/kg) in Experimental Example 1, significant reductions ($p<0.01$) in delta activity were found on days 1, 7, and 14 during long-term administration of zolpidem. Delta activities on day 21 and after withdrawal (WD) were found to be similar to the corresponding baselines (see FIGS. 11A and 11B).

Figure 11A:
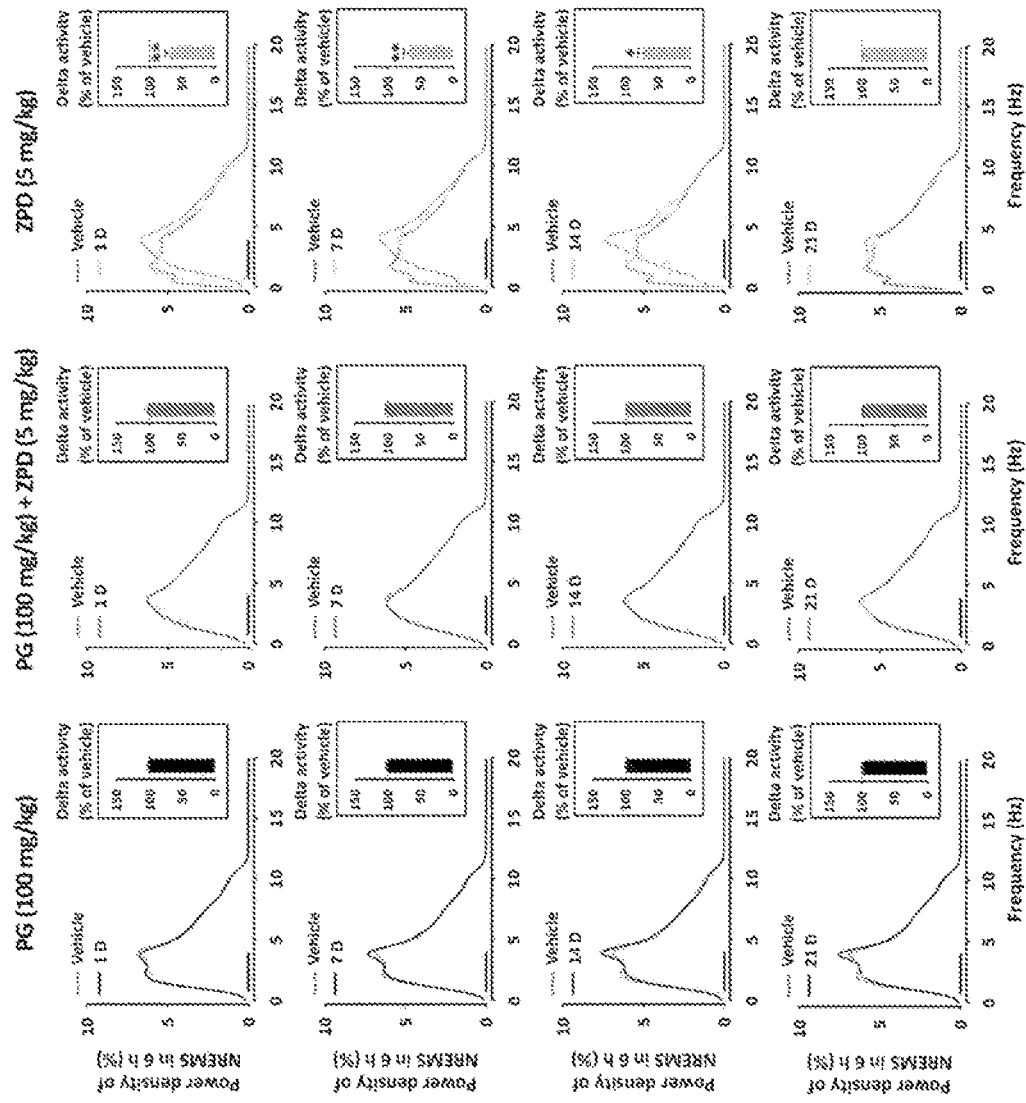
FIG. 11A shows changes in delta activity on different days during long-term administration of 100 mg/kg phloroglucinol (PG), 100 mg/kg zolpidem (ZPD), and a combination of 100 mg/kg phloroglucinol and 5 mg/kg zolpidem in Experimental Example 3.
Figure 11B:
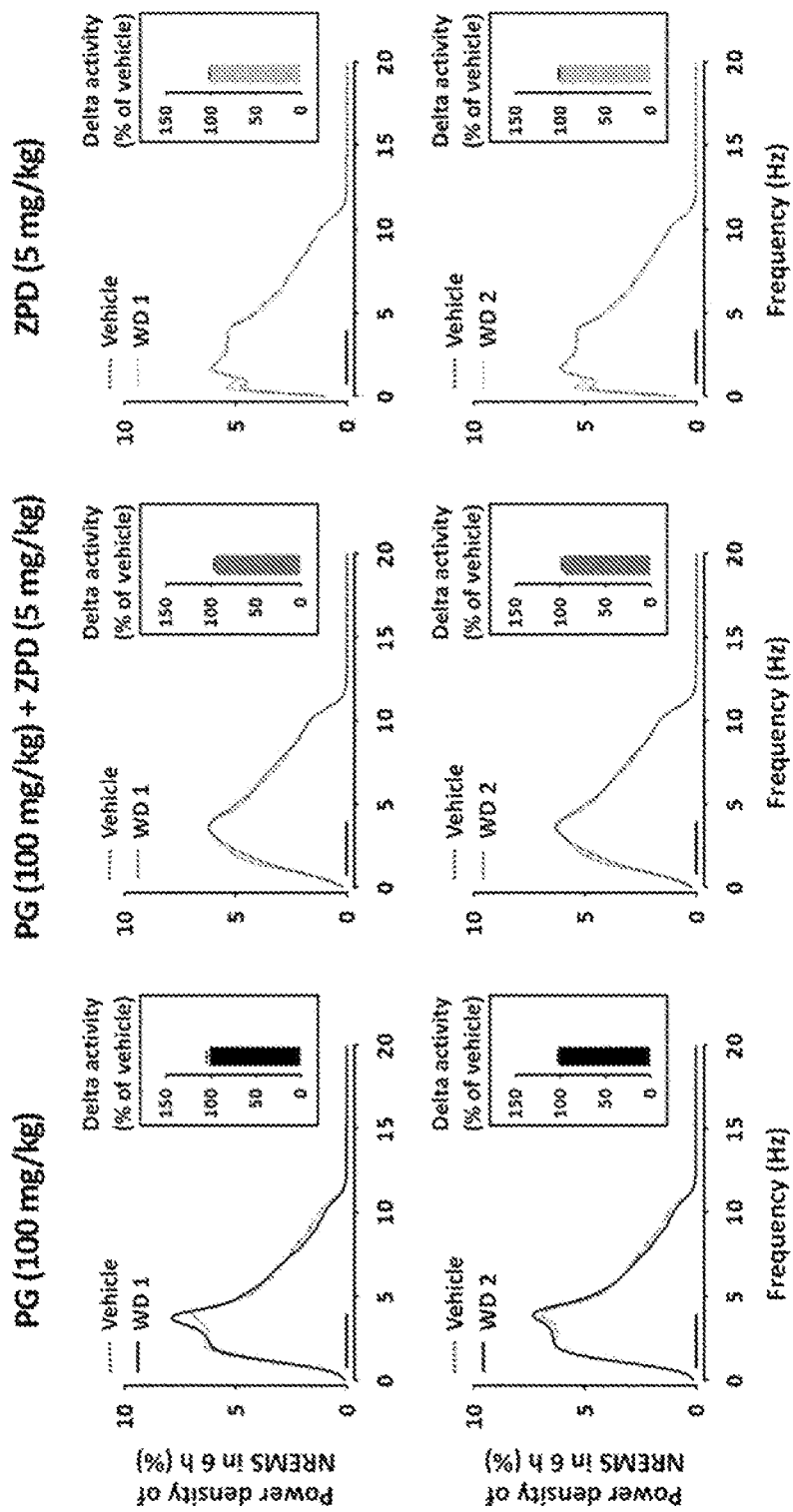
FIG. 11B shows delta activities measured on different days after withdrawal of long-term administration of 100 mg/kg phloroglucinol (PG), 5 mg/kg zolpidem (ZPD), and a combination of 100 mg/kg phloroglucinol and 5 mg/kg zolpidem in Experimental Example 3.

In contrast, when phloroglucinol (100 mg/kg) was administered alone, constant delta activities were maintained without loss over the entire long-term administration period (see FIGS. 11A and 11B).

Particularly, when phloroglucinol (100 mg/kg) and zolpidem (5 mg/kg) were co-administered, constant delta activities were maintained without loss over the entire long-term administration period. In contrast, reductions in delta activity were observed on days 1, 7, and 14 during the single administration of zolpidem (5 mg/kg) (see FIGS. 11A and 11B).

The above results show that phloroglucinol can alleviate side effects of zolpidem while maintaining the sleep-enhancing effect of zolpidem, suggesting that phloroglucinol can be used in combination with zolpidem.

Formulation examples of the pharmaceutical composition and the health functional food composition according to the present invention will be explained hereinbelow. However, these formulation examples are provided for illustrative purposes only and are not intended to limit the present invention.

Formulation Example 1. Production of Powder Preparations

| | |
|---|---|
| Phloroglucinol powder | 100 mg |
| Lactose | 100 mg |
| Talc | 10 mg |

The ingredients are mixed and filled in airtight bags to produce powder preparations.

Formulation Example 2. Production of Tablet Preparations

| | |
|---|---|
| Phloroglucinol powder | 100 mg |
| Corn starch | 100 mg |
| Lactose | 100 mg |
| Magnesium stearate | 2 mg |

The ingredients are mixed and compressed into tablets in accordance with a general method known in the art.

Formulation Example 3. Production of Capsule Preparations

| | |
|---|---|
| Phloroglucinol powder | 100 mg |
| Zolpidem | 5 mg |

| | |
|---|---|
| Crystalline cellulose | 3 mg |
| Lactose | 14.8 g |
| Magnesium stearate | 0.2 mg |

The ingredients are mixed and filled in gelatin capsules to produce capsules in accordance with a general method known in the art.

Formulation Example 4. Production of Injectable Preparations

| | |
|---|---|
| Phloroglucinol powder | 100 mg |
| Mannitol | 180 mg |
| Sterile distilled water for injection | 2974 mg |
| $Na_2HPO_4 \cdot 12H_2O$ | 26 mg |

In accordance with a general method known in the art, the ingredients are mixed and filled in ampoules to produce injectable preparations, each of which has the composition indicated above.

Formulation Example 5. Production of Liquid Preparations

| | |
|---|---|
| Phloroglucinol powder | 100 mg |
| Zolpidem | 5 mg |
| Isomerized glucose syrup | 10 g |
| Mannitol | 5 g |
| Purified water | [Appr. amount |

In accordance with a general method known in the art, the ingredients are dissolved in purified water, an appropriate amount of lemon flavor is added to the solution, the volume is adjusted to a total of 100 ml with purified water, and the mixture is filled in amber glass bottles and sterilized to produce liquid preparations.

The invention claimed is:

1. A method for suppressing intolerance to or alleviating side effects of an agonist at the benzodiazepine binding site of the GABA-A receptor, comprising administrating a pharmaceutical composition comprising phloroglucinol as an active ingredient to a patient who has intolerance to or suffers from side effects of the agonist;
   wherein the agonist is previously-administered or co-administered with the composition; and
   wherein the agonist is administered at an amount of 2 to 10 mg on a daily basis.

2. A method for treating somnipathy, comprising administering a pharmaceutical composition comprising phloroglucinol and an agonist at the benzodiazepine binding site of the GABA-A receptor as active ingredients to a patient who has intolerance to or suffers from side effects of an agonist at the benzodiazepine binding site of the GABA-A receptor.

3. The method according to claim 1, wherein the intolerance to the agonist is a reduced therapeutic effect on somnipathy resulting from long-term administration of the agonist.

4. The method according to claim 1, wherein the side effect of the agonist is one or more selected from the group of EEG delta power suppression and residual sedation.

5. The method according to claim 1, wherein the agonist is a non-benzodiazepine drug selected from the group of zolpidem, zopiclone, zaleplon, trazodone, and combinations thereof.

* * * * *